United States Patent [19]

Barnikol

[11] Patent Number: 5,994,509

[45] Date of Patent: Nov. 30, 1999

[54] METHOD FOR OBTAINING UNIFORM FRACTIONS OF HYPERPOLYMERIC HEMOGLOBINS

[75] Inventor: Wolfgang Barnikol, Mainz, Germany

[73] Assignee: Sanguibiotech AG, Mainz, Germany

[21] Appl. No.: 09/057,100

[22] Filed: Apr. 8, 1998

[51] Int. Cl.[6] .......................... A61K 35/14; A61K 38/16
[52] U.S. Cl. ...................... 530/385; 530/402; 530/412; 530/418; 530/427; 530/815; 514/6; 514/832
[58] Field of Search ..................... 530/385, 402, 530/412, 418, 427, 815; 514/6, 832

[56] References Cited

U.S. PATENT DOCUMENTS

| | | | |
|---|---|---|---|
| 4,001,401 | 1/1977 | Bonsen et al. | 530/385 |
| 4,179,337 | 12/1979 | Davis et al. | 435/181 |
| 5,252,714 | 10/1993 | Harris et al. | 530/391.9 |
| 5,312,808 | 5/1994 | Shorr et al. | 514/6 |
| 5,386,014 | 1/1995 | Nho et al. | 530/385 |
| 5,814,601 | 9/1998 | Winslow et al. | 514/6 |

FOREIGN PATENT DOCUMENTS

| | | |
|---|---|---|
| 685492 | 12/1995 | European Pat. Off. . |
| 4421742 | 1/1996 | Germany . |

OTHER PUBLICATIONS

Potzschke et al., *Advances in Expermental Medicine and Biology*, vol. 345, pp. 205–213, 1994.

Artificial Cell Blood substitutes and Immobilization Biotechnology 22 (3). 1994, 641–649, Kan, P. et al, "Application of aqueous . . . blood".

Biopolymers 23 (12). 1984, 2761–2779, Haire, R.N. et al., "The Precipitation . . . System".

*Primary Examiner*—Cecilia J. Tsang
*Assistant Examiner*—Abdel A. Mohamed
*Attorney, Agent, or Firm*—Sprung Kramer Schaefer & Briscoe

[57] ABSTRACT

A process for preparing solutions of hemoglobin hyperpolymers by fractionating hemoglobin hyperpolymers having a nonuniform molecular weight distribution according to molecular weight using a polyhydroxy compound to precipitate different fractions of hemoglobin hyperpolymers, wherein each fraction has a different but more uniform molecular weight distribution as compared to the starting hemoglobin hyperpolymers. Preferably, the polyhydroxy compound is a polyalcohol, especially polyethylene glycol.

3 Claims, 3 Drawing Sheets

METHOD FOR OBTAINING UNIFORM FRACTIONS OF HYPERPOLYMERIC HEMOGLOBINS

BACKGROUND OF THE INVENTION

1. Field of the Invention

The invention relates to a method for obtaining hyperpolymeric hemoglobins.

2. Description of Related Art

Chemical modifications of native hemoglobins for the purpose of varying the oxygen affinity or their degree of polymerization are performed with the aim of developing a synthetic oxygen carrier. This carrier is intended to support oxygen transportation by the blood in man.

Artificial oxygen carriers can be infused, for example, after an accident resulting in bleeding that is difficult to control, or in the case of a risk of infection (hepatitis, AIDS) as a substitute for a temporarily unavailable matching replacement blood. This also applies when a person is in shock due to an insufficiency of blood volume. An artificial oxygen carrier can possibly break through such insufficiency shock easier than banked blood because the preserved erythrocytes stiffen increasingly in storage and therefore have a reduced ability to pass through the capillaries, since they have to be deformed greatly while passing through the capillaries. Such artificial oxygen carriers contain no blood group antigens. Therefore they can be used universally and without cross matching beforehand.

In comparison with banked blood, an artificial oxygen carrier furthermore offers an advantage in cases in which, despite ABO and Rh factor compatibility, there is a danger of an immunological over-reaction against leukocytes. An artificial oxygen carrier, on the other hand, is entirely free of white blood corpuscles which might cause these reactions. Filtration of banked blood, through cotton for example, has proven insufficient to eliminate white blood cells. It was shown many years ago by animal tests that blood volume insufficiency shock can be combated more effectively with artificial oxygen carriers than with simple plasma expanders (review article on this subject: R. Pabst, Med. Klin. 72 (1977), 1555–1562.)

It is furthermore to be expected that chronic circulatory disturbances of a coronary, cerebral or peripheral nature can be treated effectively by means of appropriate polyhemoglobin solutions. Furthermore, oxygen deficiency conditions without circulatory deficiency, such as chronic anemia, can be treated effectively with such solutions. This is shown by the fact that oxygenated hemoglobin can yield its freely dissolved oxygen better than oxygen "packed" in erythrocytes or liposomes (see below). These indications are estimated to form ten times the market potential of "blood make-up" in the form of volume replacement. In such cases the artificial oxygen carrier must be administered as a hypooncotic additive, as blood replacement.

For the preparation of artificial oxygen carriers various approaches have been used, namely, 1. The use of emulsions of fluorinated hydrocarbons in which oxygen is very soluble (for a review: Issues from the Vth International Symposium on Blood Substitutes, Artificial Cells, Blood Substitutes, and Immobilization Biotechnology 22 (1994).) This method, however, has the disadvantage that when fluorinated hydrocarbons are used tissue reactions occur due to macrocytic cells; of decisive importance here is a critical size of the vesicles, which is about 0.3 $\mu$m.

2. The microencapsulation of concentrated hemoglobin solutions in phospholipid vesicles to form so-called artificial erythrocytes or "hemosomes" (Review article: Gaber et al., Encapsulation of Hemoglobin in Phospholipid Vesicles; Preparation and Properties of a Red Cell Surrogate in "The Red Cell, Sixth Ann Arbor Conference," G. J. Brewer (publisher); Alan R. Liss, Inc., New York, (1984), 179–190).) Here the danger of macrocytic activation is involved. As in par. 1, a change of the artificial emulsifiers into the (dynamic) membranes of the cell is probable, so that the function of these membranes can be disturbed.

3. The preparation of appropriate hemoglobin solutions, also with covalent bonding of the hemoglobin to dextran, by which renal excretion is said to be reduced; dextrans tend, however, to stimulate the immune system.

4. Crosslinking the hemoglobin molecules with one another likewise prevents renal excretion. In addition, there is an advantage over the dextran-bound hemoglobins of a higher oxygen binding capacity. Recently it has been possible by crosslinking to obtain soluble hyperpolymeric hemoglobins whose colloid osmotic pressure with respect to standard pressure (32 mbar) in the presence of the necessary concentrations is negligible (Potzschke et al., Advances in Experimental Medicine and Biology; N. Back et al. (Eds.) Vol. 345, 205–213, Plenum Press New York 1994). This approach combines most of the advantages referred to.

The various approaches mentioned are reflected in the following patents:

Patent DE-OS 24 17 619 describes, for example, the synthesis of polymerized, linked hemoglobin as a substitute plasma protein, hemoglobin linked with dicarboxylidat [sic] being prepared.

Patent DE-OS 27 14 252 describes the preparation of hemoglobin linked with pyrodoxal phosphate.

Patent DE-OS 30 29 307 relates to an artificial carrier which is made by covalent linking of a polysaccharide, dextran for example, with cell-free hemoglobin. Patent BE-PS 838 933 describes the preparation of a water-soluble, linked, polymerized hemoglobin by the reaction of free hemoglobin with a polyfunctional linking agent, followed by stopping the reaction with inactivating agents. A polymeric hemoglobin is made with a molecular weight of 61,000 to 1,000,000 daltons.

U.S. Pat. No. 4,001,401 relates to a linked, polymerized hemoglobin as a plasma expander with a molecular weight of 64,000 to 1,000,000 daltons, which is obtained with the linking agents, glutaraldehyde, hexamethylene diisocyanate or butadiene diepoxide.

European Patent EP 0 201 618 describes a method for the preparation of extra-high molecular weight, compact, soluble polymers of hemoglobin from a highly concentrated solution of monomeric hemoglobin. These polymers of high molecular weight are referred to as hyperpolymers.

In Patent DE-PS 37 14 351, this process is simplified in that erythrocytes are used directly, and the crosslinking agent no longer needs to be added in a lipid phase.

In the preparation of suitable modified hemoglobin solutions for use in clinical practice, the necessity arises of keeping the viscosity of the solution as low as possible. The viscosity of the blood co-determines the so-called total peripheral resistance of the organism. If it is too great, the circulatory system will no longer tolerate it. In particular, an additional burden is placed on the heart. In the case of dissolved hyperpolymers and also hemoglobin polymers, such problems are intensified if polymerization to chain molecules occurs.

Einstein's viscosity law says that uniformly large spheres in a fluid have a minimal viscosity regardless of their radius. This viscosity depends solely on the overall volumetric content of the spheres in the solution. For the viscosity of the solutions to remain low, the polymer molecules must accordingly be so compact—say "spherical"—that with the viscosity of the plasma at a minimum, a maximum amount of the oxygen carrier can be transported.

Therefore, to minimize the viscosity it is important to be able to produce oxygen carrying molecules that are as uniform as possible. Such molecules are also found in nature, e.g., in the earthworm. The uniformity of the molecules and the achievement of a very high molecular weight is a requirement of an artificial oxygen carrier which will satisfy the requirement of a negligible colloidal osmotic pressure. To achieve this, at least all of the hyperpolymeric hemoglobin content in question must be removed.

With EP Patent 0 201 618 and German Patent 37 14 351, the problem of linking hemoglobin to form compact, but soluble, giant molecules can be considered solved. The methods described therein, however, lead to a hyperpolymer mixture with a wide distribution of the molecular weight and a severely disproportional increase of the viscosity with increasing concentration (Bernikol and Burkhard, Adv. Exp. Biol. Med. 248 (1989) 335–340), especially in the range of concentration in which the artificial carrier is to be used.

SUMMARY OF THE INVENTION

The present invention is addressed to the problem, therefore, of creating a process by which molecularly uniform hemoglobin hyperpolymers, but of different molecular weight, can be separated from a known hemoglobin hyperpolymer solution with a wide distribution of the molecular weights.

It would thus be possible to set the molecular weight of an artificial oxygen carrier very high in order to satisfy the requirement of a negligible colloidal osmotic pressure. Although it is indeed possible to reduce the viscosity by separating the monomers and oligomers by ultrafiltration, the amount of the reduction is not sufficient.

BRIEF DESCRIPTION OF THE DRAWINGS

The invention will now be described in more detail with reference to the drawings, wherein.

DESCRIPTION OF THE PREFERRED EMBODIMENTS

Figure 1:
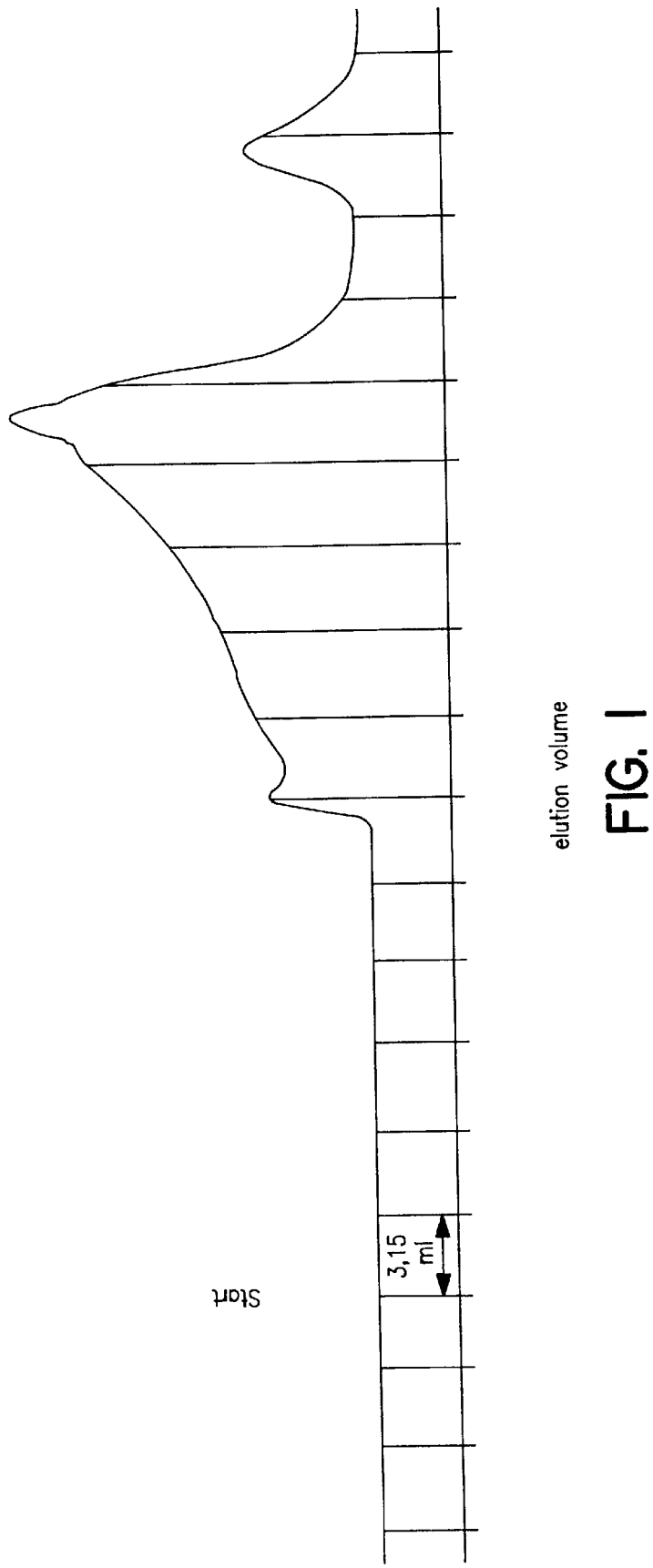
FIG. 1 is a chromatograph of the starting product of Example 1.

DE 38 41 105 C2 describes a method for obtaining molecularly uniform fractions of polymerized hemoglobin, which makes use of fractional dissolution. Use is made of the fact that during the crosslinking reaction the polymeric hemoglobin precipitates first, but a few hours later it passes almost entirely into solution, and surprisingly it is the polymers of low molecular weight that dissolve first. It was found, however, that the fractions of the solution are of insufficient uniformity, which works against the need for a low viscosity in the polyhemoglobin solution, as well as a sufficiently low oncotic pressure. Ideally it is polymers of the most uniform kind, of about 10 to 20 monomeric units, i.e., hemoglobin molecules, that are needed.

DE 44 18 973 A1 describes a method of preparing molecularly uniform hemoglobins by the combination of various separation processes, namely ultrafiltration, fractional precipitation with ammonium sulfate, chromatography, and partial dissolution. Ultrafiltration, however, is an additional expensive technical process which increases the denaturing of the delicate molecule—and which, as regards production with a high yield, also has the disadvantage that it makes the process expensive. Also, the combined use of the said processes promotes an increased formation of dyshemoglobins (e.g., methemoglobin) which are no longer capable of binding. Furthermore, the many working steps involved in ultrafiltration reduce the yield, so that production becomes very cost intensive, inasmuch as the starting material for the crosslinking reaction would have to be high-purity hemoglobin.

DE 44 21 742 A1 describes a method of preparing molecularly uniform hemoglobins by a staged reaction with a bi- or multifunctional crosslinking agent. At least five dimerization steps are necessary in order to be able to obtain a sufficiently high molecular weight. The chromatographic separating processes necessary in each step, however, cause the yield to decrease almost exponentially, not to mention a great increase in the dyshemoglobin content.

The methods of the state of the art for obtaining uniform hyperpolymeric hemoglobins therefore have the disadvantages of complex technical procedures, denaturation of the delicate molecules, formation of undesired byproducts, irregular distribution of molecular weights, insufficient polymerization, contamination with monomers and oligomers, and expensive purification processes. And lastly their output is in some cases too low.

Consequently, the present invention is addressed to the problem of providing a method for the preparation of a modified, polymerized hemoglobin, which will yield a stable, highly crosslinked, very uniform hyperpolymeric hemoglobin with a great ability to transport oxygen and a low dyshemoglobin content. It is to be technically simple as well as low in cost, it is to have a high separating ability, and it is to provide uniform fractions of the polymers for all molecular weights of the polymeric hemoglobins.

The need thus existed for developing a fractionation method having the said properties.

Known methods of fractionation cannot be used for the reasons given. Gel chromatography is also an expensive method, which furthermore gives but low yields. Fractional precipitation of proteins with alcohols, as performed to obtain specific plasma proteins is successful only when it is a question of different proteins of uniform molecular weight and identical molecule shape; according to applicant's own experiments the method is not successful in the case of crosslinked hemoglobins. The same applies to the known precipitation with ammonium sulfate.

The above-stated problem is solved by the invention by the fact that the hyperpolymeric hemoglobins can be precipitated with polyethylene glycol. In particular, it was surprisingly found that this polyalcohol permits a fractional precipitation of the hyperpolymeric hemoglobins which leads to the desired narrow fractions of these polymers. It is thus found that the solubility of the crosslinked hemoglobins in mixtures of polyethylene glycol and water depends greatly on the degree of the linking of the covalently coupled hemoglobins. The invention will now be demonstrated by the following examples.

EXAMPLE 1
Crosslinking the Hemoglobin

In this example of practice a bovine hemoglobin is involved, which is crosslinked with diisothiocyanatobenzene sulfate (DIBS). Heparinized bovine blood (25,000 I.U. per 500 ml) is thrice washed with 0.15 M of $NaHCO_3$ and then centrifuged for 30 minutes at 20,000 g. The packed erythrocytes are lysed by freeze shock; this yields an approximately 30% hemoglobin solution. 200 ml of this solution can be deoxygenated by stirring and flooding over with moistened nitrogen for 24 h at 4° C. After the addition of a $10x$ molar amount of DIBS, dissolved in dimethylsulfoxide, the hemoglobin is crosslinked in 16 hours, after which the reaction with lysine HCl at pH=8.3 (2 ml 1M per 0.45 g Hb) has ended, then the polymer is dissolved with distilled water for 24 h in ten times the volume of the specimen. FIG. 1 shows the chromatogram of the starting product prepared in this manner for the precipitations.

EXAMPLE 2
Separation of the High-molecular Weight Portions from the Starting Product (see Example 1) by Precipitation with Polyethylene Glycol 6000 (PEG).

Figure 2:
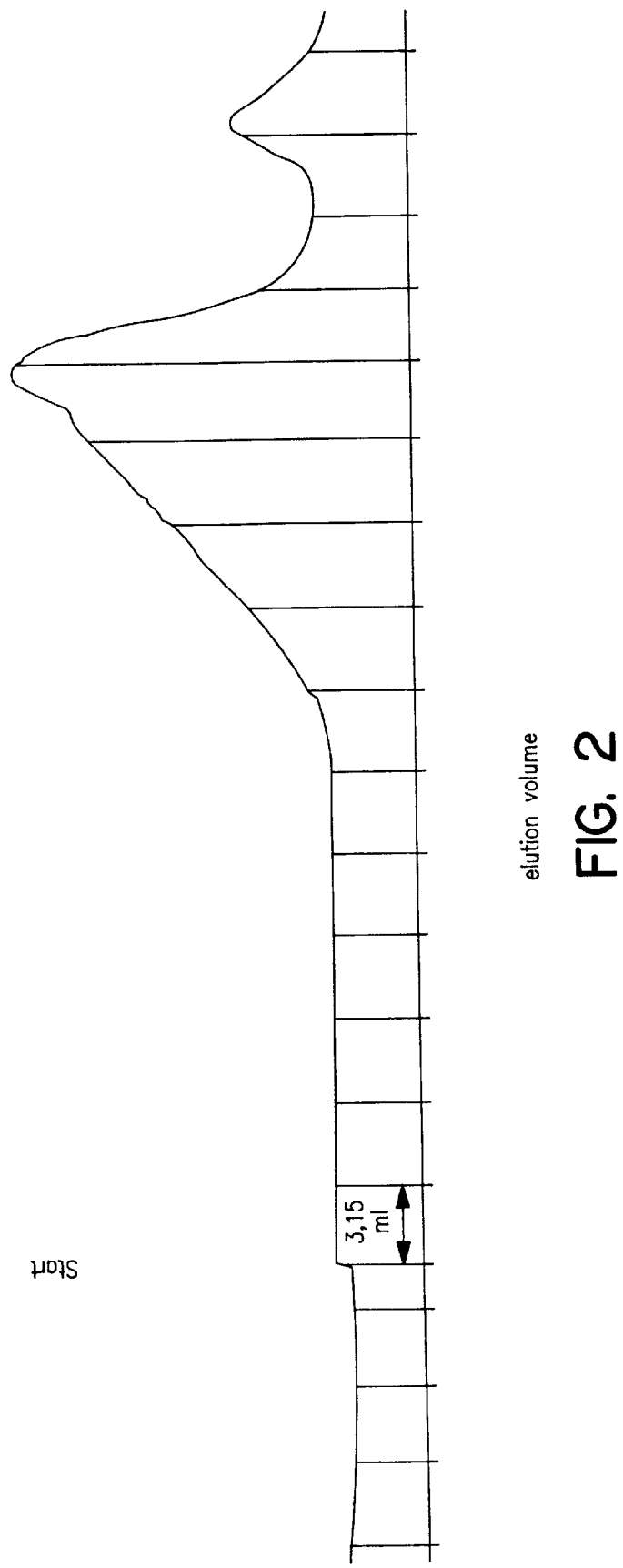
FIG. 2 is a chromatograph of the hemoglobin polymer in the supernatant of Example 2.

6.5 g of a PEG solution (50 g PEG and 50 g of BiKu) was added to 43.5 g of a 1.7% Hb solution of the starting product (pH=7.9), mixed and left to precipitate for 2 hours at 4° C. Then a centrifugation was performed for 30 minutes at 15,000 rpm. The yield of the supernatant was 70%. FIG. 2 shows the chromatogram of the hemoglobin polymer in the supernatant.

EXAMPLE 3
Fractional Precipitation with PEG from the Supernatant of Example 2.

Figure 3:
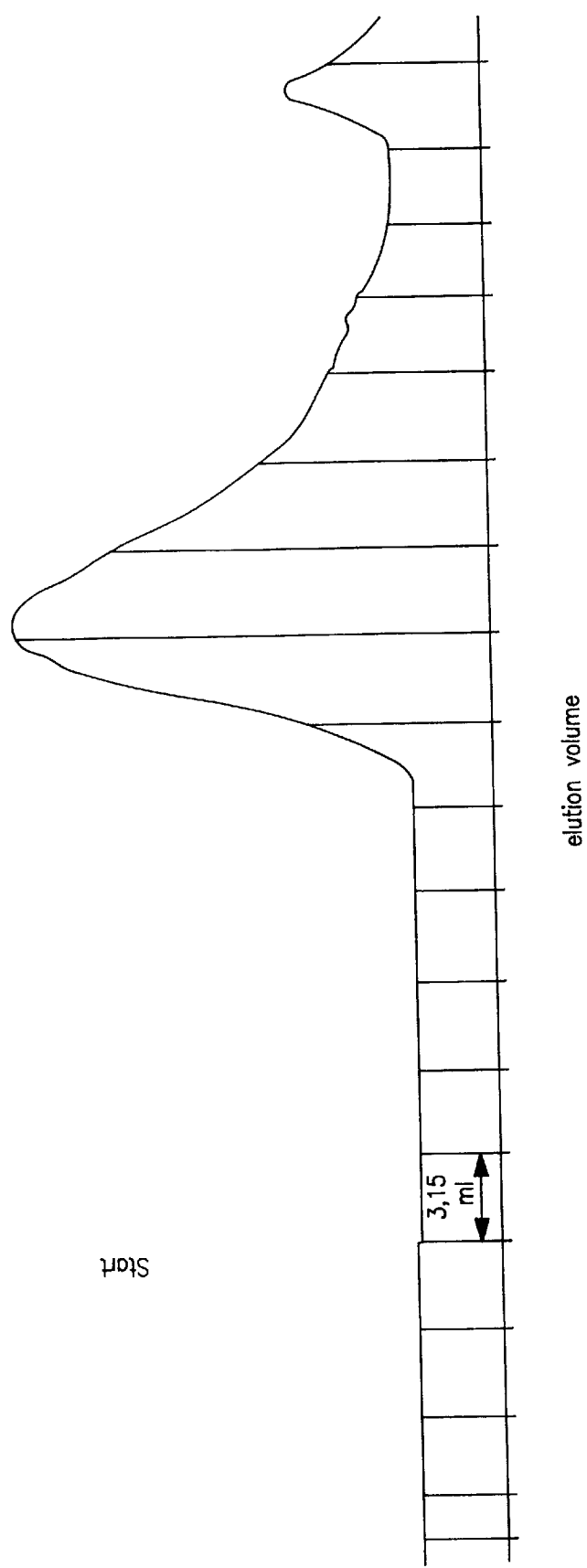
FIG. 3 is a chromatograph of the dissolved precipitate of Example 3 and then on the very next line insert the following heading at the left-hand margin.

To 9.82 g of the supernatant liquid, 0.18 ml of a PEG solution (50 g of PEG and 50 g of BiKu) was added and the mixture was allowed to react for 16 hours at 4° C. This was followed by strong centrifugation, one washing of the precipitate with about 12% PEG solution in BiKu, and then dissolution of the precipitate with stirring in Biku. FIG. 3 shows a chromatogram of the dissolved precipitate.

BiKu: 125 mmol/1 NaCl; 4.5 mmol/1 KCl

I claim:

1. A process for preparing solutions of hemoglobin hyperpolymers, said process comprising fractionating hemoglobin hyperpolymers having a nonuniform molecular weight distribution according to molecular weight using a polyhydroxy compound to precipitate different fractions of hemoglobin hyperpolymers, each fraction comprising hemoglobin hyperpolymers having a different but more uniform molecular weight distribution as compared to said hemoglobin hyperpolymers having a nonuniform molecular weight distribution.

2. A process according to claim 1, wherein the polyhydroxy compound is a polyalcohol.

3. A process according to claim 2, wherein the polyalcohol is polyethylene glycol.

* * * * *